United States Patent
Yardley (10) Patent No.: US 6,168,580 B1
(45) Date of Patent: Jan. 2, 2001

(54) ANTIMICROBIAL DEVICE AND METHODS FOR LONG-TERM CATHETERS

(75) Inventor: James V. Yardley, Centerville, UT (US)

(73) Assignee: Iontophoretics Corporation, Bountiful, UT (US)

(*) Notice: Under 35 U.S.C. 154(b), the term of this patent shall be extended for 0 days.

(21) Appl. No.: 09/276,843

(22) Filed: Mar. 26, 1999

(51) Int. Cl.[7] .................................................. A61M 25/00
(52) U.S. Cl. ............................... 604/265; 604/20; 604/21
(58) Field of Search ..................................... 604/265, 266, 604/280, 20, 21, 114, 523, 526; 607/115, 116, 121, 122, 127

(56) References Cited

U.S. PATENT DOCUMENTS

| | | | |
|---|---|---|---|
| 4,676,782 | 6/1987 | Yamamoto | 604/175 |
| 4,847,049 | 7/1989 | Yamamoto | 422/24 |
| 4,906,238 | * 3/1990 | Greenfield et al. | 604/266 |
| 4,973,320 | * 11/1990 | Brenner et al. | 604/265 |
| 5,324,275 | 6/1994 | Raad . | |
| 5,409,467 | 4/1995 | Raad . | |

* cited by examiner

Primary Examiner—Glenn K. Dawson
Assistant Examiner—Jennifer Maynard
(74) Attorney, Agent, or Firm—Gale H. Thorne; Paul S. Evans (57) ABSTRACT

An antimicrobial device which is adaptably affixable to a large variety of commercially available catheters. Preferably, the device employs a pair of metal ion emitting electrodes which are at least partially disposed within an insertion site of the catheter and which are pulsed with alternating potentials to electrolytically elute ions into surrounding tissue to build an antiseptic zone about the insertion site. The device comprises an insertion sleeve and associated jacket which is slidably affixable to the indwelling catheter and a self-contained battery power source and electronics unit. The unit supplies power for the electrolytic action and for electronics which time the period and width of potential signals for the electrolysis. Through alternate elution and deposition of ions back and forth between the electrodes, long term indwelling catheter efficacy is assured. Period activation also increases length of battery life. The electronic unit also has easily seen indicators which signal state of battery power. While this device is usable in most catheter procedures, its use is particularly applicable for long term indwelling catheter applications.

21 Claims, 10 Drawing Sheets

ANTIMICROBIAL DEVICE AND METHODS FOR LONG-TERM CATHETERS

FIELD OF INVENTION

This invention is related to antimicrobial devices, processes and materials for catheters which are used to provide access to blood and other physiologic vessels and, especially, for such processes in which catheters are left in situ over long periods of time and are therefore likely subject to becoming a pathway for infection.

DESCRIPTION OF RELATED ART

Problems associated with medical devices which come into contact with infection-sensitive areas of the body and become introducers of infection are well known in contemporary medicine. In particular, indwelling catheters are known to be dangerous conduits by which infection is introduced over time. The longer the time indwelling catheters are in place, the greater the likelihood of resulting serious infection. Invasive medical devices such as central venous catheters (CVCs), peripherally inserted catheters (PICCs), endotracheal catheters and urinary catheters are known sources of infection as a result of microbial colonization.

Even though a large number of infections are the result of a small number of organisms, (e.g. *Staphylococcus epidermidis, Staphylococcus aureus* and *Candida albicans*), the number is neither limited nor well defined. It is now well known in the medical art that organisms may and can change to make contemporary chemical antimicrobial agents less effective and even ineffective as time passes.

Antimicrobial creams or coatings, such as chlorhexidine, may not only be becoming ineffective, but may themselves be contaminated before application. Still more of a dilemma is the growing tendency to lengthen the period of use of long-term indwelling catheters. For this reason, even more effective products which use heavy metals (e.g. gold, silver and copper) to provide antimicrobial activity, are not effective for a long enough period of time when indwelling catheters are used for extended periods. Shortcomings of known current approaches, whether it be by chemical or by elution of heavy metals, generally do not provide protection of sufficiently extended periods to provide complete protection for all uses of extended use indwelling catheters, an example of which is found in the use of central venous catheters (CVCs).

In addition, catheter technology in general and CVC technology specifically has matured to the point where many different catheter types and sizes are available to fulfill many general and special medical procedure needs. An attempt to compete with any established catheter manufacturer, much less with the total set of manufacturers as a body would likely be unsuccessful by a neophyte catheter manufacturer.

BRIEF SUMMARY AND OBJECTS OF THE INVENTION

In brief summary, this novel invention alleviates serious problems related to microbial infections resulting from implantation of catheters used to provide access to blood and other physiologic vessels, especially of those catheters which are implanted for a long period, e.g. three months or longer. The instant invention includes apparatus and methods for applying an attachable integral jacket and sleeve subassembly about an indwelling catheter at an insertion site for the purpose of reducing and preventing microbial infections associated with catheterization procedures.

In one embodiment, the invention is effectively applied to techniques and apparatus disclosed in U.S. Pat. Nos. 5,409,467, issued to Raad et al., Apr. 25, 1995 and 5,324,275 issued to Raad et al., Jun. 28, 1994 (generally referenced herein by Raad). In this case, the invention provides opportunity for electrically exciting a pair of electrodes, disposed parallel to one another and powered by a power source and electronics which are an inherent part of the jacket. So disposed and powered, the electrodes elute ions which are displaced from one electrode to the other to provide an effective antimicrobial zone of influence.

Such is substantially different from teachings disclosed in Raad. Raad discloses affixing a helical electrode and electrode connections directly to a catheter. While such is possible and practical for a given catheter manufacturer to affix electrodes and connections as a part of a manufacturing process, it may be impractical to so affix the electrodes to a catheter subsequent to catheter manufacture by another vendor, and especially impractical to apply electrodes and connections after catheter sterilization.

As an example, one contemporary intravascular catheter manufacturer makes and markets as many as seventy different catheter types and models. It would be highly unlikely that a start-up catheter manufacturer could enter the catheter market and effectively compete with a reasonably few number of catheter types and/or models. It may be even less likely that a company which is proficient in manufacture of devices made in accordance with the instant invention also be effective in making catheters. For this reason, an important feature of the invention is the ability to affix elements of the invention to a catheter as an added feature preparatory to use.

Various embodiments of the invention are possible, including impregnating an entry or percutaneous sleeve of the device with antimicrobial substances. Generally, the device consists of two separate parts, although it may be made from one or more parts. The first part includes a catheter jacket and sleeve subassembly from which the antimicrobial agent is eluted. The jacket and sleeve are formed to fit firmly about an indwelling catheter in such a manner that the catheter attachment may be engaged by snapped or threaded containment. In this manner, an unmodified catheter (standard catheter), regardless of catheter variety, vendor or application may be used with the invention. In any case, the sleeve provides access to antimicrobial material through a catheter entry orifice and about the indwelling catheter itself in the vicinity of the entry orifice. In a device which is directly associated with the method of Raad, the sleeve utilizes two parallel conductive elements which are operably connected to a power source and related electronics which energize the conductive elements to create and induce oligodynamic activity proximal to the indwelling catheter and which are disposed in the jacket. A weaving structure is disclosed whereby conductive, ion emitting wires are maintained in a substantially parallel orientation along longitudinal radial segments surrounding the captured catheter.

The second part of a two part device is a second subassembly which is releasibly affixed to the jacket part preferrably by a snap action. This action also, preferably, firmly affixes the jacket and therefore the sleeve to the indwelling catheter. The second part includes a self-contained battery power source and electronics associated with controlled elution of the antimicrobial substance. To transfer material disseminating power to conductive wires, complementary connections to connectors of the first part are conjoined when the second part is affixed to the first part. For use with devices related to Raad, the electronics provide a periodic, alternating and/or pulsed charge, using low current drain electronics for prolonging the life of the energizing battery.

Accordingly, it is a primary object to provide a device which may be affixed to unmodified catheters in the vicinity of a percutaneous or orifice entry site and which supplies antimicrobial substances at the site for the purpose of reducing infection attributed to catheter use.

It is a further object to provide a device which may be affixed to a long term indwelling catheter and provide effective antimicrobial activity for an extended period, which may be three months or longer.

It is an important object to provide an electrical circuit for eluting heavy metal ions in a predefined and controlled manner.

It is another object that the electrical circuit be provided in a self-contained package which is a part of the device.

It is still another object that the electrical circuit include a battery.

It is an object that heavy metal ions be eluted from more than one elongated electrode as taught by Raad.

It is an object that the electrical circuit provide alternating polarity of potentials disposed upon a pair of electrodes such that ions are alternately eluted and then deposited upon each electrode to extend life of the device to provide an effective antimicrobial zone of influence.

These and other objects and features of the present invention will be apparent from the detailed description taken with reference to accompanying drawings.

DETAILED DESCRIPTION OF THE ILLUSTRATED EMBODIMENTS

Figure 1:
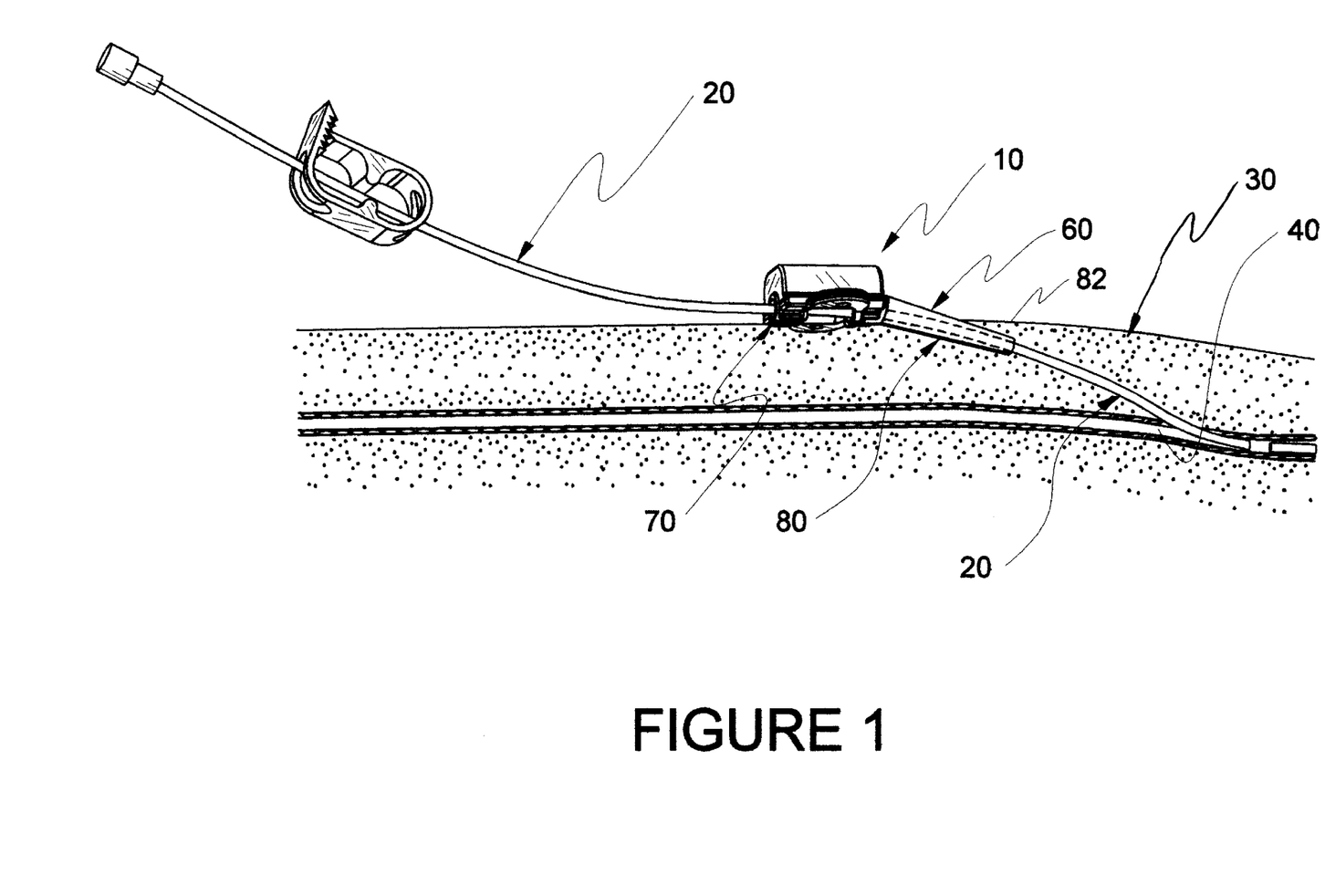
FIG. 1 is a perspective of a catheter assembly comprising an indwelling catheter, an attachable antimicrobial subassembly and associated locking cap subassembly securely affixed to the antimicrobial subassembly, with the catheter in place in a vessel.

In this description, the term proximal is used to indicate a segment of an element or device which is normally closest to the object of a sentence describing its position. The term distal refers to the other end. Reference is now made to the embodiments illustrated in FIGS. 1–10 wherein like numerals are used to designate like parts throughout. As seen in FIG. 1, an antimicrobial device 10, which is made in accordance with the instant invention disclosed herein, is generally securely, but releasibly affixed to an indwelling catheter 20. It is important to note that catheter 20 may be any type of catheter used, in this case for percutaneous entry through tissue 30 into a vessel 40 of a patient. Prior to securing device 10 in place relative to catheter 20 and tissue 30, device 10 is slidably disposed about catheter 20 to facilitate proper placement.

While this percutaneous application pertains to CVC and other blood vessel related catheter procedures, one skilled in the catheter art would understand that devices used in accordance with the instant invention would also apply to other medical procedures, of which use of urinary catheters is an example. In broad terms, such devices should find application to any number of alternative medical devices suitable for use with infection-sensitive areas of the human and animal physiology.

Figure 2:
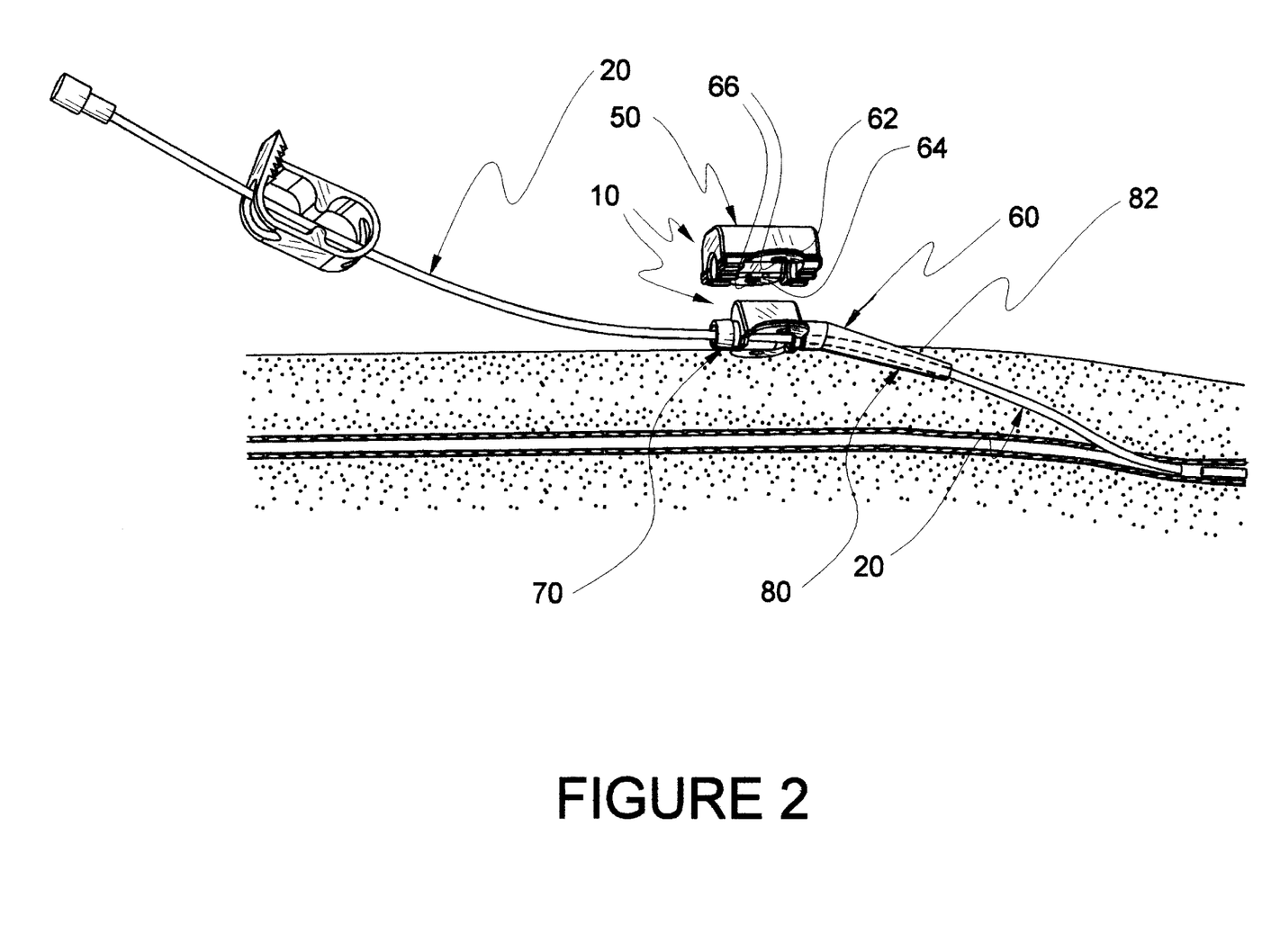
FIG. 2 is a perspective of the catheter assembly of FIG. 1, with the associated locking cap subassembly displaced to permit the antimicrobial subassembly to be more clearly seen.
Figure 3:
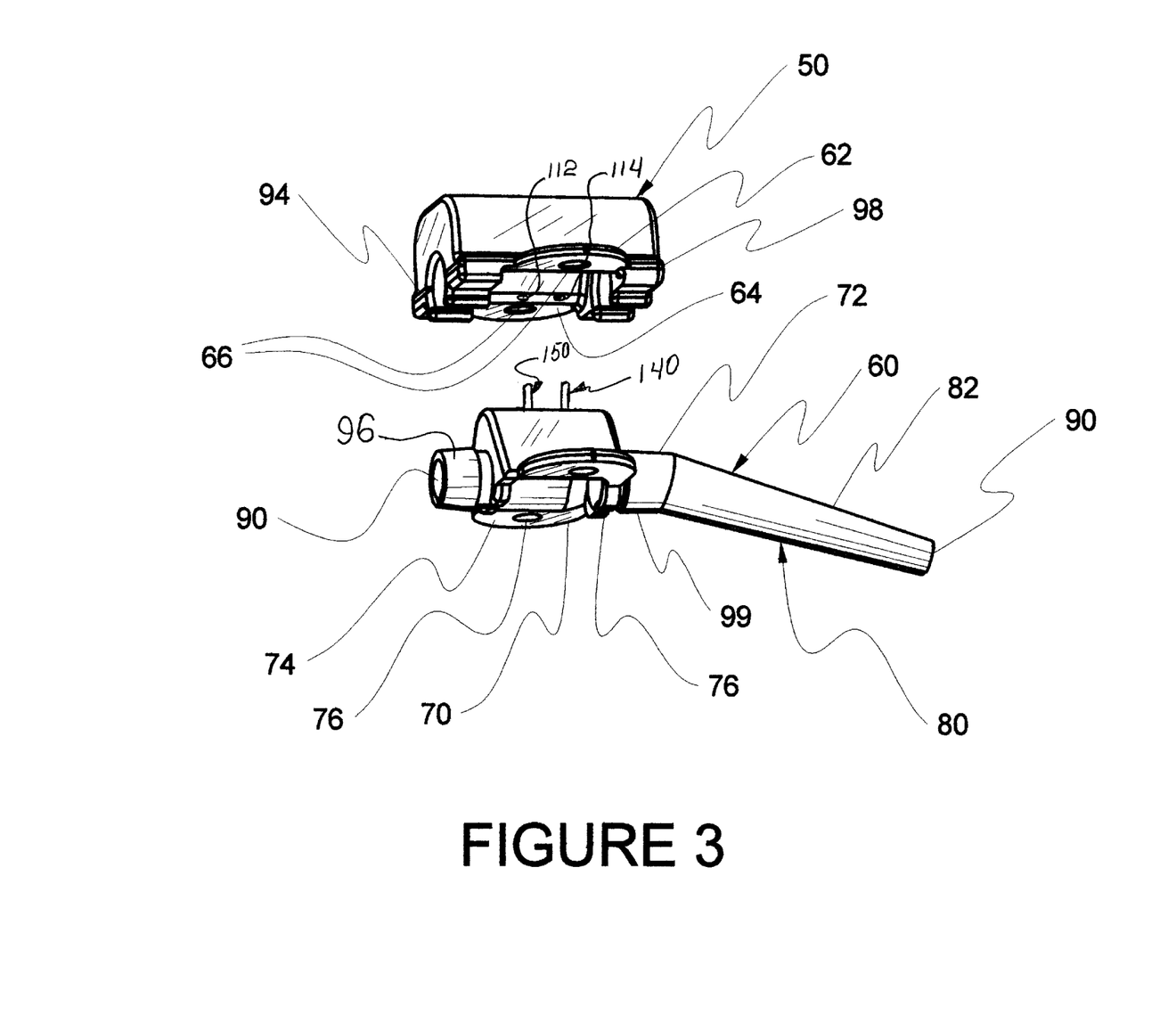
FIG. 3 is an exploded perspective view of primary parts of the antimicrobial subassembly and associated catheter.

Referring to FIG. 2, a separable portion of device 10, a locking cap subassembly 50 is lifted from a jacket and sleeve subassembly 60 to permit clearer visualization of the two parts 50 and 60 which, in combination, make device 10. Subassembly 50 comprises a pair of suture wings 62 and 64. Each suture wing 62 and 64 comprises a suture hole 66.

Jacket and sleeve subassembly 60 comprises a jacket portion 70 and a sleeve portion 80. As is more clearly seen in FIG. 3, jacket portion 70 also comprises a pair of suture wings 72 and 74. Wings 72 and 74 each comprise a suture hole 76.

Sleeve portion 80 is an elongated hollow cylindrical part having a distal part 82 which slopes inferiorly to facilitate tracking direction of catheter 20 insertion as seen in FIGS. 1 and 2. Part 82 should be disposed about catheter 20 and partially inserted into the catheter insertion site for effective use. In combination, portions 70 and 80 comprise a common lumen 90 through which catheter 20 is threaded or into which catheter 20 is snapped to slidably affix jacket and sleeve subassembly 60 to catheter 20.

Figure 5:
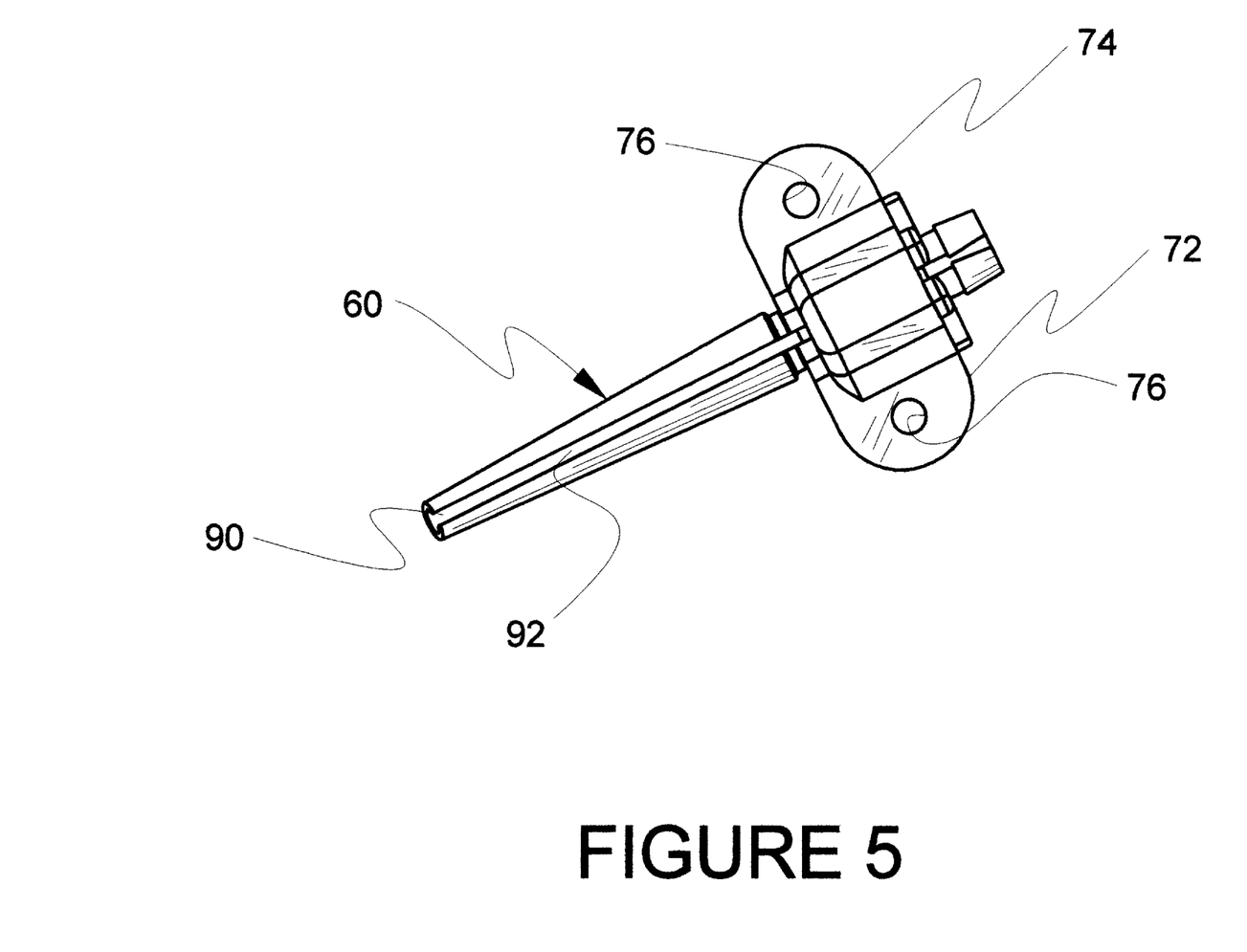
FIG. 5 is a bottom elevation of the antimicrobial subassembly.

While it is important that jacket and sleeve subassembly 60 be slidably displaceable along catheter 20, it is equally as important that when catheter 20 and jacket and sleeve subassembly 60 emplacement at an insertion site is complete, readying indwelling catheter 20 for use in a medical procedure, that device 10 is securely disposed and immovable relative to catheter 20 and, likewise, that indwelling catheter 20 and device 10 are immobilized relative to the insertion site. For the purpose of permitting slideable displacement of subassembly 60 along catheter 20, an elongated slit 92 is disposed along the length of lumen 90, as seen in FIG. 5. By virtue of slit 92, lumen 90 is sufficiently open to permit indwelling catheter 20 to slide relative to subassembly 60. However, should slit 92 be substantially narrowed by squeezing jacket portion 70 laterally, catheter 20 is gripped and held fast within lumen 90. For this reason, lumen 90 of jacket and sleeve subassembly 60 should be sized to conform with the outside diameter of a catheter 20 selected for use with device 10 in a medical procedure. Jacket and sleeve subassembly should be made from a compliable material which is relatively inert, such as a synthetic resinous material from which catheters are made.

Referring again to FIG. 3, locking cap subassembly 50 comprises a proximally disposed arcuate snap fitting 94 which is sized and configured to snap about a proximal section 96 of jacket portion 70 and squeeze lumen 90 and slit 92 to tightly grip indwelling catheter 20 without occluding it. Similarly, locking cap subassembly 50 comprises a distally disposed arcuate snap fitting 98 which is sized and configured to snap about a distal section 99 of jacket portion 70 for the same purpose as snap fitting 94. In this manner, snapping locking cap subassembly 50 onto jacket and sleeve subassembly 60 securely affixes device 10 to indwelling catheter 20.

When subassembly 50 is so affixed to subassembly 60 suture wings 62 and 64 are aligned with suture wings 72 and 74, respectively, such that respective holes 66 are aligned with respective holes 76. This alignment permits suturing the suture wings in place thereby securing catheter 20 at an insertion site and affixing the most distal portion of catheter 20 relative to the insertion site. Note that a secure attachment may be made using holes 76 alone. Such a mode of anchoring a catheter is common in catheter emplacement art. As locking cap subassembly 50 must be able to crimp jacket portion 70 about indwelling catheter 20, locking cap subassembly 50 is preferably made from a relatively strong and rigid synthetic resinous material such as a medical grade polycarbonate.

While sleeve portion 80 is particularly well suited to introduction of elongated heavy metal wires, it may also be impregnated with various antimicrobial substances that have been found effective in reducing catheter-related infections. Some of these include antibiotics such as menocycline and rifampin and/or antimicrobials such as chlorihexidine and silver sulfadiaizine, which have been shown to be highly efficacious in significantly reducing the rate of catheter colonization and preventing catheter related bacteremia. The scope of this invention includes applying existing and future antimicrobial technologies to a catheter attachable device in a low cost environment achieved by attaching the device to already commercially available catheters. In this manner, a general requirement for impregnating all catheter devices, when only a portion of the devices should be so customized can be effectively ameliorated. When applying the invention to devices related to the disclosure of Raad, antimicrobial effectiveness is dramatically improved.

Figure 4:
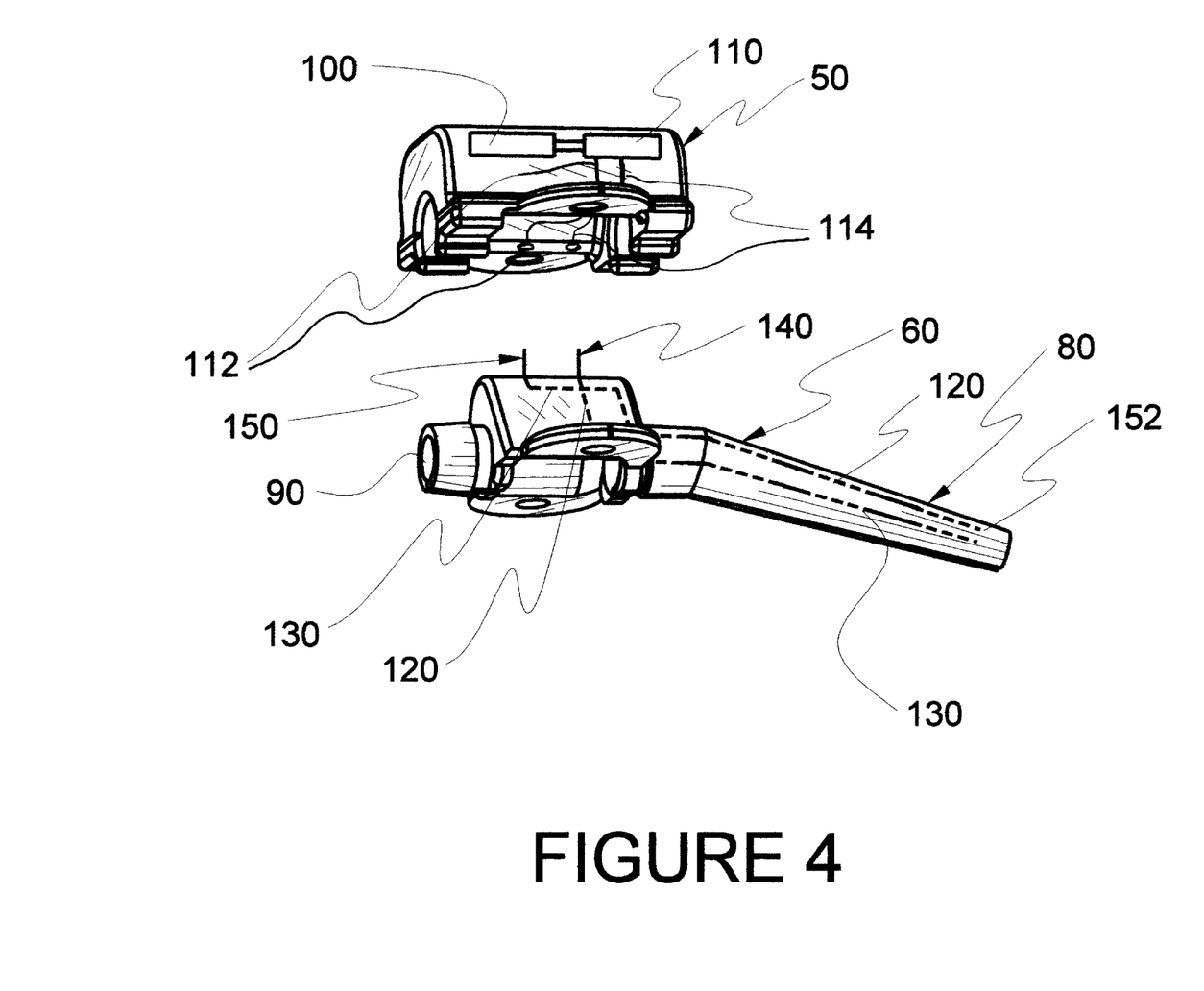
FIG. 4 is a block diagram of the parts seen in FIG. 3, wherein distributed conductive elements are seen in the antimicrobial subassembly and electrical and control components are seen disposed in the locking cap subassembly.

As disclosed in Raad, an effective antimicrobial device is achieved by alternating oppositely polarized voltage potentials across a pair of parallel (helically wound) electrodes preferably made from a heavy metal such as silver. Attention is now directed to FIG. 4 wherein, in schematic format, device 10 is seen to comprise a battery 100 and associated electronics 110 housed within locking cap subassembly. Electrically connected to electronics 110 are a pair of electrical connecting sockets 112 and 114.

Jacket and sleeve subassembly 60 comprises a pair of strands of heavy metal wire (120 and 130) which are disposed in a predetermined configuration in sleeve portion. Proximally, wire 120 electrically communicates with a connecting pin 140. Wire 130 similarly communicates with a connecting pin 150. Pins 140 and 150 are disposed to interconnect with socket-to-electronics connections 114 and 112, respectively, to provide a controlled voltage signal from electronics 110 as powered by battery 100. Further, each wire communicates with lumen 90 and exterior surface 152 of sleeve 80 as disclosed in detail hereafter.

Figure 6:
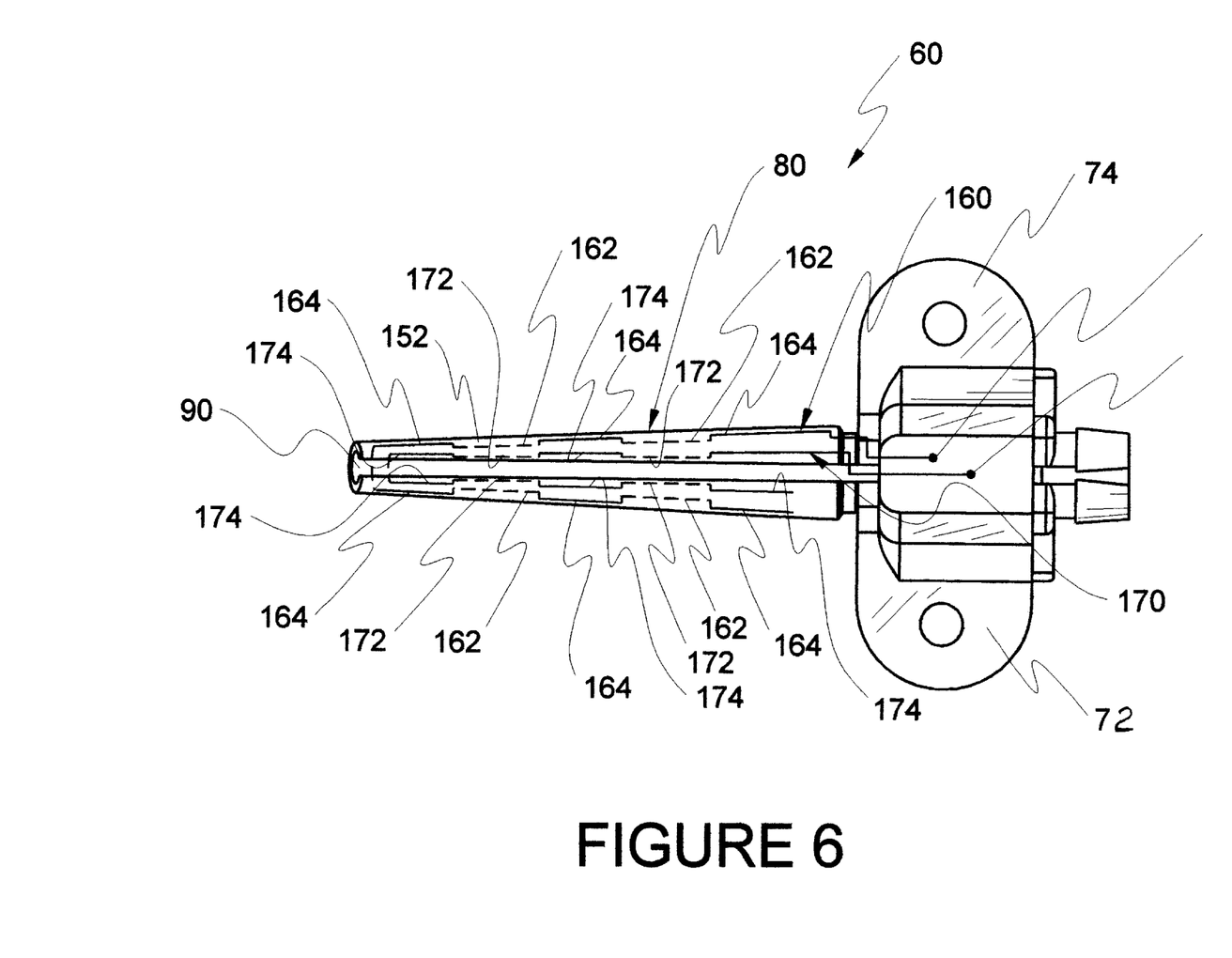
FIG. 6 is a block diagram of the antimicrobial subassembly seen in FIG. 5 wherein exemplary pathways for linear distribution of antimicrobial substances are seen.
Figure 7:
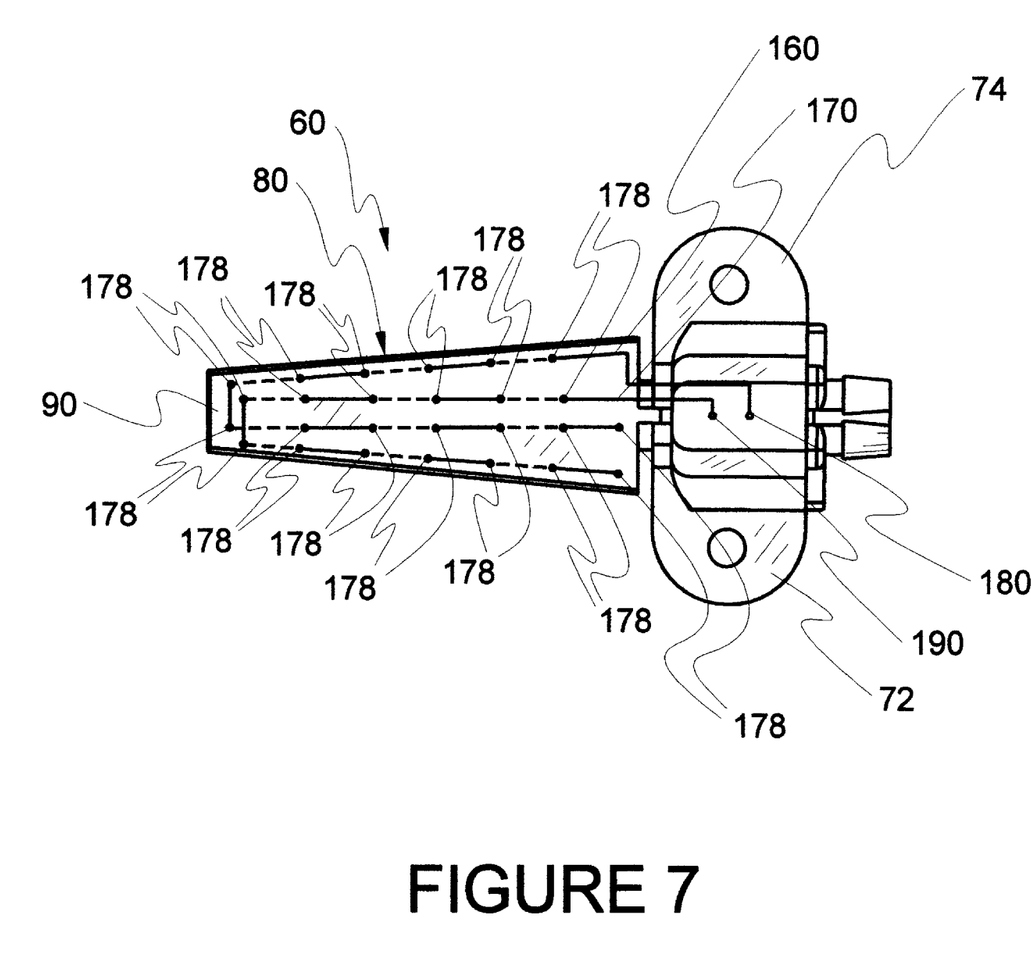
FIG. 7 is a detail of the block diagram of FIG. 6 wherein a distal section of the antimicrobial subassembly is displayed in planar format for clearer visibility of the pathways.

Reference is now made to FIGS. 6 and 7 wherein one mode of distributing wires 120 and 130 is seen. As seen in FIG. 6, a pathway 160 for wire 130 is represented by a linear sequence of dashed lines 162 and undashed lines 164, In similar fashion, a pathway 170 for wire 120 is represented by a linear sequence of dashed lines 172 and undashed lines 174. Pathways 160 and 170 are more clearly seen in FIG. 7 wherein sleeve 80 is seen in a planar format. Dashed lines 162 and 172 reside on sides which are distal to a side viewed. For this reason, dashed lines represent pathways inside lumen 90 in FIG. 6, while dashed lines in FIG. 7 represent pathways on surface 152. Undashed lines 164 and 174 are disposed on surfaces viewed in FIGS. 6 and 7. Therefore undashed lines 164 and 174 are on surface 152 in FIG. 6 and undashed lines 164 and 174 are a part of exposed lumen 90 surface 176 in FIG. 7. As disclosed in Raad, wires 120 and 130 should be disposed on substantially parallel paths. Wires 120 and 130 are woven along paths 160 and 170, respectively, alternately being threaded along surface 152 and then upon surface 176 such that ions produced by elution of material from the wires are distributed about each surface. For this purpose a pattern of holes 178, which provide access for wires 120 and 130 being threaded through sleeve 80, are distributed in a predetermined pattern throughout sleeve 80. Of course, other paths, for example paths which are more similar to a helix pattern, may be used within the scope of the invention.

To connect wires 130 and 120 to pins 140 and 150, pathways 160 and 170 originate proximally at communicating holes 180 and 190, respectively. When laying out a pattern for wires 120 and 130, care should be taken to assure the wires are evenly distributed along surfaces 152 and 176, are substantially mutually parallel, do not cross or touch each other and are in a relatively constant spaced relation one to the other. When selecting material for wires 120 and 130, both electrical conductive properties and oligodynamic properties should be considered. Heavy metals including gold, copper, silver, platinum, iron, aluminum and zinc are recommended. Silver is particularly preferred due to its demonstrated antimicrobial effectiveness. If material used for sleeve 80 is both water and ion permeable, wires 120 and 130 may be imbedded with the walls of sleeve 80. Similarly, it may be preferred to lay patterns of wire pathways by processes used in printed circuit board manufacture. All of these modes are within the scope of the instant invention.

Figure 8:
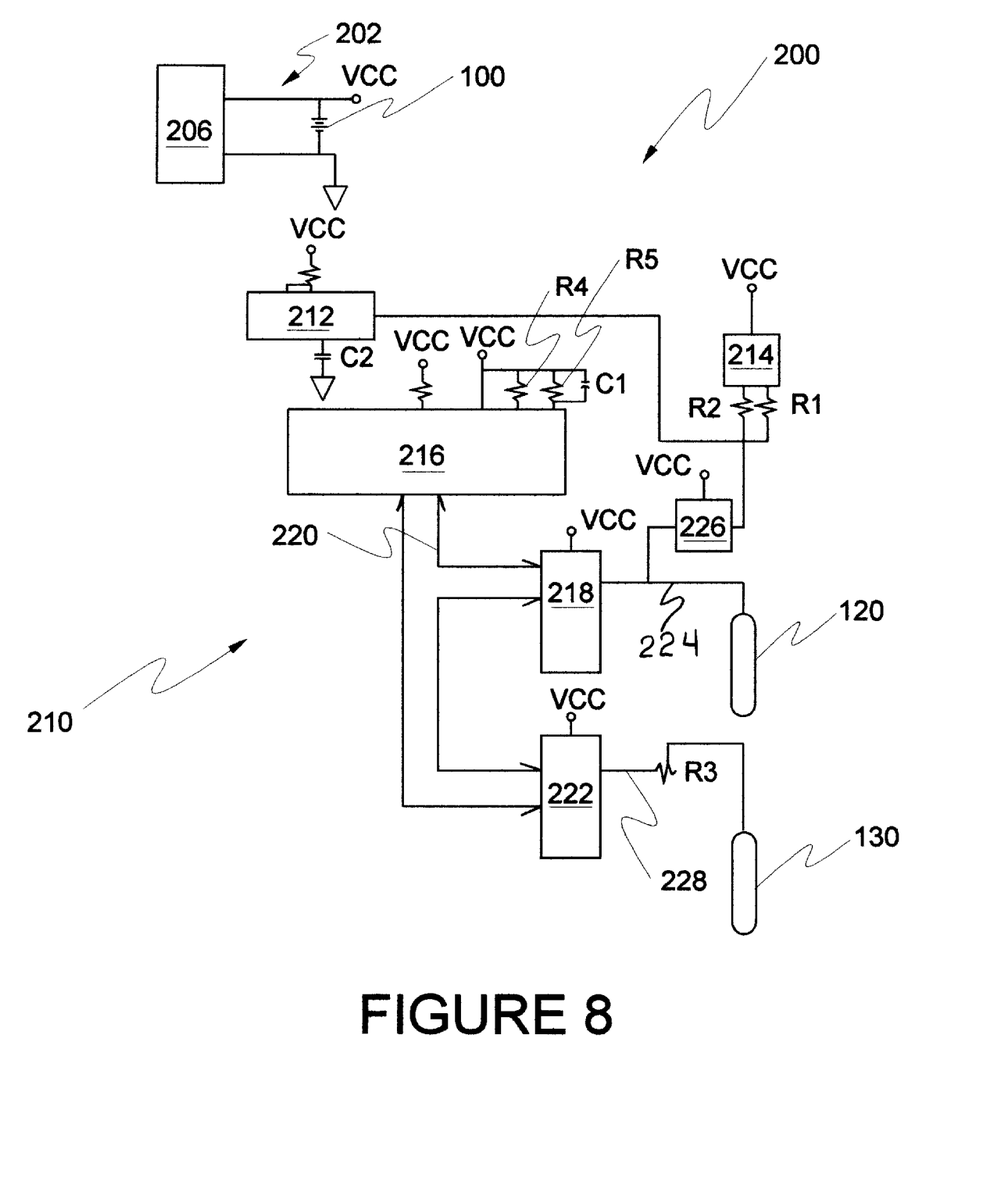
FIG. 8 is a block diagram of an exemplary electrical circuit which may be used to apply alternating and/or pulsed potentials to conductive elements of the antimicrobial subassembly.
Figure 9:
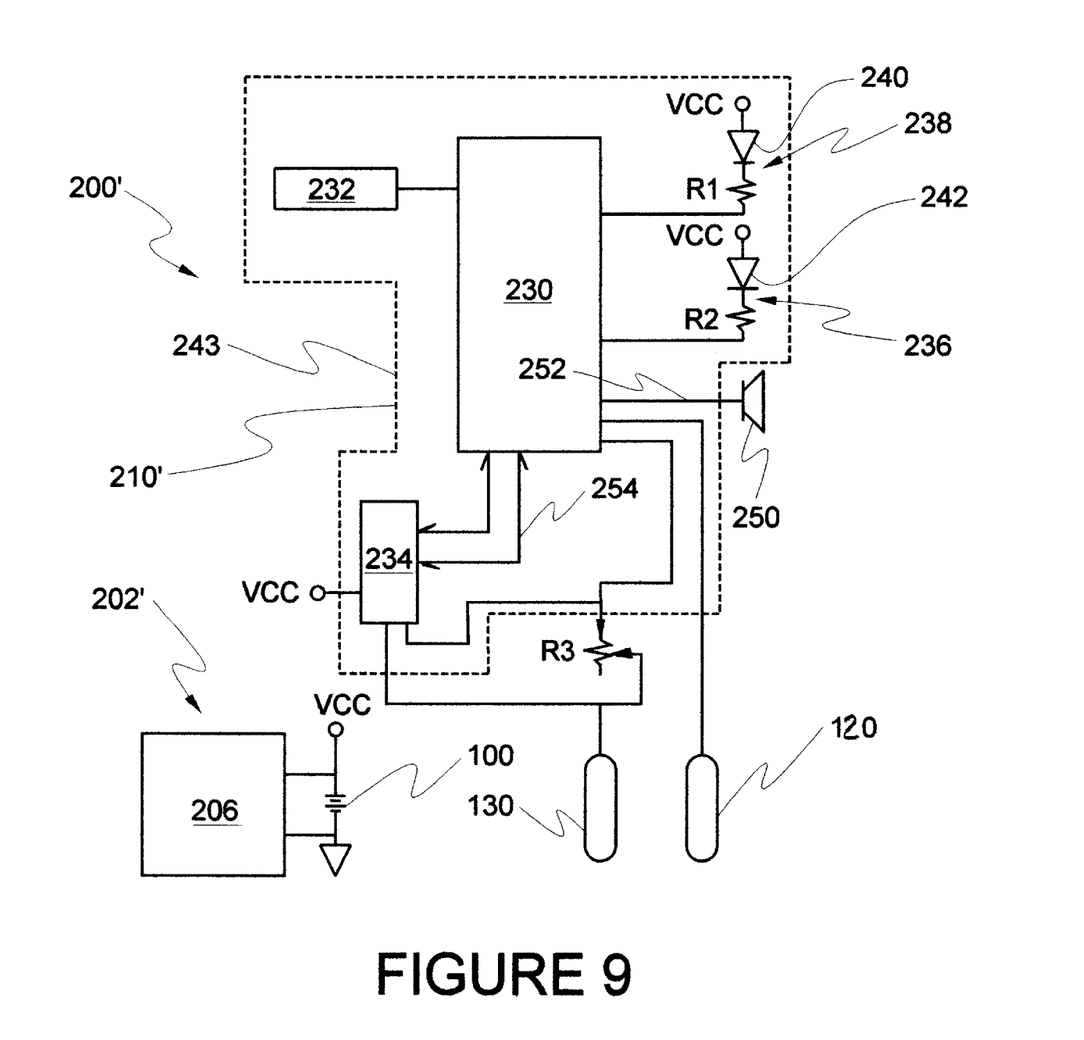
FIG. 9 is a block diagram of another exemplary electrical circuit used in the same manner as the circuit of FIG. 8, but which provides a customized microprocessor low current drain integrated circuit.
Figure 10:
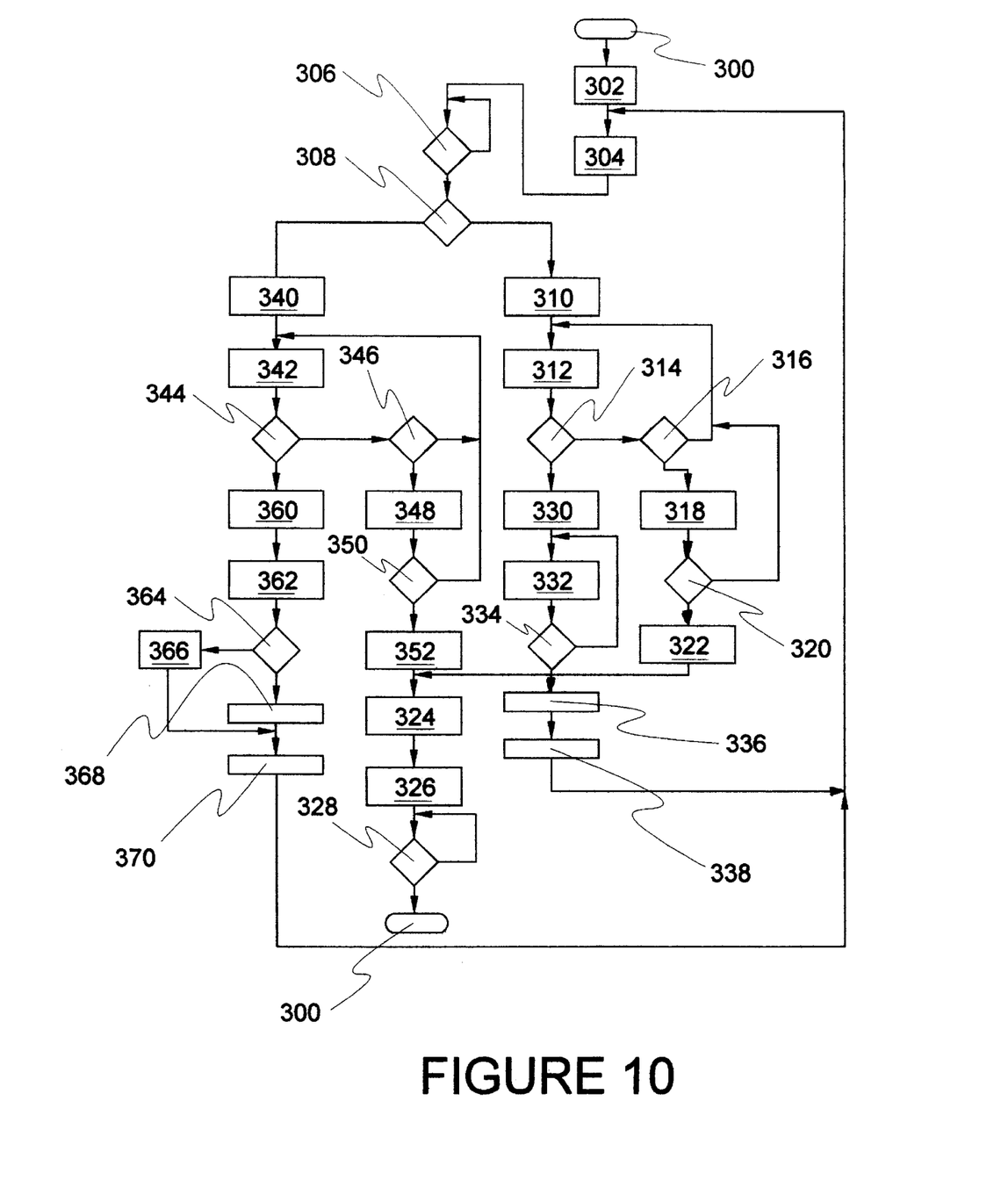
FIG. 10 is a block diagram of a flow chart for microprocessor operation of the exemplary electrical circuit seen in FIG. 9.

Attention is directed to FIGS. 8–10 wherein schematics for circuits and flow diagrams for providing voltage to wires 120 and 130 are seen. FIG. 8 shows one embodiment of a low current drain charging circuit 200. Circuit 200 comprises a power source circuit 202 comprising a battery 100 and optional solar cell 206. In addition, circuit 200 comprises a charging circuit 210.

Charging circuit 210 comprises power reset and battery monitoring element 212 which is connected through resistor R1 to LED chip 214. Further, charging circuit 210 comprises counter 216 which is interconnected to a first state decoder 218 via bus 220. Counter 216 is also interconnected to a second state decoder 222 via bus 220. Bus 220 communicates bit data from counter 216 to each of the state decoders 218 and 222.

State decoder 218 decodes three counter states, such as states 0, 1, and 2 of counter 216. As an example, when counter 216 is counting at a one second per count rate, decoder 218 produces a three second digital pulse upon an output line 224. The three second output pulse is communicated to one of the wires 120 or 130, in this case, for example, 120 will be selected. The three second pulse is also sent via line 224 to a pulse generator 226 which communicates with LED chip 214 through resistor R2.

State decoder 222 decodes three counter states, such as 30, 31 and 32 of counter 216. In this manner decoder 222 produces a three second digital pulse upon an output line 228 which is directed through a current limiting potentiometer R3 to the second wire 130 of wire pair 120 and 130.

Solar cell 206 may be used when external energy from any applicable source is available and may be used to provide charging power to battery 100. Solar 206 may be selected from a number of solar cells currently commercially available, based upon desired power output and size.

Battery 100 may be a lithium battery rated at 3.6 volts. For non-rechargeable applications, a Tadiran model IL-2186 may be used, although any applicable battery may be used within the scope of the invention, dependent upon desired current, power and size considerations. Battery 100 cathode is connected to ground and battery 100 anode is connected to provide VCC potential.

Counter 216 is a sixty stage counter, though other counters may be used. As an example, counter 216 may be a Maxim ICM7260 integrated circuit component. This particular component has a internal clock generator based upon external RC components. These components are seen as R4, R5 and C1 and are selected to produce a clock period of one second.

Power reset and battery monitoring element 212 may be a National Semiconductor LP3470 device. Element 212 monitors battery 100 voltage and turns on a warning LED (e.g. a red LED) when battery power is low. As seen in FIG. 8, element 212 is connected to ground through a capacitor C2.

The components of FIG. 8 have been selected because of their low power requirements for the purpose of extending battery life. In long term indwelling catheter applications, a battery life of six or more months is desirable. These and other components which may be used in the invention are readily identifiable by those who are skilled in the electronic circuit design art.

As used in this application, counter 216 is a divide by sixty device and is pulsed by a one second pulse. For this reason, counter 216 generates count states 0 though 59. States 0–2 are decoded by decoder 218 to produce a three second pulse which is used to activate wire 120. As well, decoder 222 decodes states 30–32 to produce a three second pulse. Note that during states 0–2 a positive potential is imposed upon wire 120 which produces metallic (e.g. silver) ions which flow to wire 130 and subsequently current flows through current limiting resistor R3 to decoder 222. Conversely during states 30–32, a three second pulse causes ions to flow in the opposite direction from wire 130 to wire 120. Current is limited throughout the three second pulse to be typically in the range of 20 microamperes, for adequate antimicrobial activity.

Output of pulse generator 226 is typically a pulse of 100 millisecond duration. Connected through resistor R2, the 100 millisecond pulse causes a green LED of LED circuit 214 to be illuminated once each minute to indicate normal operation of circuit 200. Note that LED circuit 214 is a red/green LED indicator. For this purpose, a ROHM SNL020 LED integrated circuit may be used.

A second embodiment of a low current drain charging circuit (numbered 200') is seen in FIG. 9. Circuit 200' comprises a power source circuit 202' comprising a battery 100 and optional solar cell 206. In addition, circuit 200' comprises a charging circuit 210'.

Charging circuit 210' comprises a digital processor 230, a clocking circuit 232, an analog to digital converter 234 and a pair of LED display circuits, 236 and 238. LED display circuit 238 comprises resistor R1 and a red LED 240. LED display circuit 236 comprises resistor R2 and a green LED 242.

The circuits enclosed by dashed line 243 are preferably included into a single customized large-scale integrated circuit. Preferably, low current drain IC technology should be used to further lengthen battery life. Note that it is possible to include power source circuit 202' in the same customized large scale integrated circuit. In like manner, circuit 202' may be built from individual logic and circuit blocks. Those skilled in the circuit design art will understand that numerous customized integrated circuits are possible within the invention to be used for the purpose of elongating the life of battery 100.

Clocking circuit 232 is a 30 second timer which generates a short lived pulse minimally greater than three seconds to awaken processor 230 from a sleep mode. When awakened to a processing mode, processor 230 alternatively applies power to one of the wires 120 or 130.

Microprocessor 230 is retained in sleep mode for slightly less than twenty-seven of each thirty second cycle. At each awakening, processor 230 is programmed to apply a potential to a wire not previously powered in its last awakened state. In other words, upon a first awakening processor 230 may apply power to wire 120. In the next awakening state, processor 230 will apply power to wire 130. Thus power is preferably applied for a three second interval once each thirty seconds, with power being applied to each wire once each minute.

Processor 230 also monitors system operation. Based upon detected signals, the processor enables operation of each LED 240 and 242 (LED 240 emitting a red color for a battery or other alert indicator and LED 242 emitting a periodic green color to indicate proper periodic operation). An optional piezoelectric tone generator 250 is connected through line 252 to processor 230 whereby a tone may be emitted as an audible alert indicator.

Analog to digital (A/D) converter 234 is connected to processor 230 via a bus 254. A/D converter 234 monitors both sides of R3 to enable changes in current between wires 120 and 130 to be determined. A/D converter 234 also is used to monitor VCC (power output of battery) to determine when battery power falls to an unacceptable level. As indicated above, power or current failures are indicated by illumination of LED 240. Different patterns of pulses from LED 240 permits various alert indications which may comprise battery low, low wire 120 to wire 130 current and other failure modes.

Microprocessor 230 may be programmed as seen in the flow diagram of FIG. 10.

The components of FIG. 9 should be selected for low power operation for the purpose of extending battery life. In long term indwelling catheter applications, a battery life of six or more months is desirable. These and other components which may be used in the invention are readily identifiable by those who are skilled in the electronic circuit design art.

A method for controlling operation of circuit 200' is depicted in a flow diagram in FIG. 10. As may be noted in FIG. 10, processor 230 monitors the voltage of battery 100 via A/D converter 234 and current through wires 120 and 130 and ultimately pulses red LED 240 and green LED 242 in predetermined patterns to indicate status of operation of circuit 200'. Red LED 240 is pulsed once each minute when battery 100 voltage level drops below a predetermined safe, yet still operable, level. When battery 100 voltage drops below such a level, red LED 240 is continuously enabled to indicate necessity for exchanging battery 100. As earlier disclosed, tone generator 250 may be employed to indicated a similar alert condition. In routine operation, green LED 242 is illuminated for a short duration, once each minute. When sensing current through wires 120 and 130 indicates an operational anomaly, both LED's 240 and 242 are enabled to indicate a need for immediate service.

Reference is now made to FIG. 10, where a power on reset 300 begins an initialization sequence 302. Following initialization sequence 302 charging circuit 210' is programmed through a wait loop 304 to a sleep state which resides within decision block 306.

Upon a trigger from clocking circuit 232, a decision block 308 is entered wherein a determination is made whether to apply charging power to wire 120 or wire 130 based upon information stored in processor 230 concerning last energized wire. If the determination causes path to block 310 to be followed, the wire (as an example wire 120) is enabled. A subsequent action of block 312 measures current through wires 120 and 130. A next decision block 314 determines whether or not a signal transmitted along wire 120 has been enabled for three seconds, if not program sequence continues to decision block 316 where the earlier disclosed determination of a momentary anomaly is made. If there is no anomaly, flow continues to block 312. If an anomaly is detected, sequencing continues to block 318 where a record is accumulated of detected anomalies. From block 318, sequencing continues to decision block 320 wherein the number of accumulated anomalies is tested. If the number is below a predetermined level, program flow continues to block 312. If the number exceeds or is equal to the predetermined level, sequencing continues to block 322 wherein both LED's 240 and 242 are illuminated and program sequences to block 324.

Entry into block 324 causes an alarm to be sounded if optional tone generator 250 is included in circuit 200'. In next succeeding block 326, sleep mode is disabled which causes the alarm to be sounded indefinitely until a reset occurs. Wait for reset is accomplished in next sequence decision block 328. A reset of charging circuit 210 drives entry into reset block 300 with subsequent path to block 302.

If the test for passing of the three second period within decision block 314 is successful, power to wire 120 is removed via block 330. After removal of power to wire 120 in block 330, green LED 242 is enabled in block 332 in combination with decision block 334 which times illumination of LED 242 through an approximate 100 millisecond period. At the end of the 100 millisecond period, LED 242 is disabled in block 336. Next the information stored in processor 230 which is relative to selection of next wire (in this case wire 130) is changed to gate flow through decision block 308 appropriately in block 338. From block 338 program flow is to block 304.

Should entry into decision block 308 direct program flow to block 340 for the purpose of applying charging power to wire 130 (per the earlier example of applying charging power to wire 120 through block 310), charging power is applied to wire 130 in block 340. A subsequent action of block 342 measures current through wires 120 and 130.

A next decision block 344 determines whether or not a three second period has passed. From block 344 program sequence continues to decision block 346 where the earlier disclosed determination of a momentary anomaly is made. If there is no anomaly, flow continues to block 342. If an anomaly is detected, sequencing continues to block 348 where a record is accumulated of detected anomalies. From block 348, sequencing continues to decision block 350 wherein the number of accumulated anomalies is tested. If the number is below a predetermined level, program flow continues to block 342. If the number exceeds or is equal to the predetermined level, sequencing continues to block 352 wherein both LED's 240 and 242 are illuminated and program sequences to block 324. Logical sequence through and following block 324 is as disclosed above.

If the test for passing of the three second period within decision block 344 is successful, power to wire 130 is removed via block 360. After removal of power to wire 130 in block 360, battery 100 voltage is measured in block 362 through A/D converter 234 in combination with decision block 364 which checks battery level against a preset minimum operating voltage. If the voltage in battery 100 is below the acceptable value, red LED 240 is enabled in block 366. Note that this enabling yields a constantly illuminated red LED 240. Other flow paths could be readily generated by one skilled in computer programming art to provide a flashing LED 240 which warns of a less critical alert. In subsequent block 368, any prior enabling of red LED 240 is disabled. Note that program flow from block 366 is to block 370 which is also subsequent to flow through block 368. Block 370 switches selection from wire 130 to wire 120 for next loop through decision block 308. Flow from block 370 is to block 304.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An antimicrobial device which is affixed to an indwelling catheter, said device comprising:

a sleeve and jacket assembly comprising an elongated sleeve part with a jacket part securely affixed thereto;

said sleeve part comprising a pair of spatially separated electrodes disposed in a predetermined pattern such that, when said sleeve part is at least partially disposed within an electrically conductive medium, ions eluted by electrolysis from one of said electrodes and attracted to the other of said electrodes creates an effective antimicrobial zone of influence within said medium about said electrodes;

said jacket part and said sleeve parts of said jacket and sleeve assembly cooperatively comprising a pathway through which the indwelling catheter is slidably disposed;

said jacket part further comprising extensions of each of said electrodes and a first electrical connector for communicating electrical power signals with a second electrical connector; and a locking cap assembly comprising a primary power source and a control circuit for applying power in a predetermined sequence and polarity to said electrodes;

said locking cap assembly further comprising a fitting, which releasibly but securely affixes said locking cap assembly to said sleeve and jacket assembly and further compressively affixes said sleeve and jacket assembly to the indwelling catheter disposed in said pathway thereby obviating displacement of the indwelling catheter relative to the sleeve and jacket assembly, and the second electrical connector which completes an electrical circuit to said electrodes through said first connector when the locking cap assembly is affixed to said sleeve and jacket assembly.

2. An antimicrobial device according to claim 1 wherein said locking cap assembly comprises a monitor for determining status of said power source.

3. An antimicrobial device according to claim 2 wherein said locking cap assembly comprises video displays for reporting measured electrical status of said device.

4. An antimicrobial device according to claim 2 wherein said locking cap assembly comprises an audio generator for audibly reporting measured electrical status of said device.

5. An antimicrobial device according to claim 1 wherein said locking cap assembly comprises an auxiliary power source for augmenting effective life of said primary power source.

6. An antimicrobial device according to claim 5 wherein said auxiliary power source is a solar cell.

7. An antimicrobial device according to claim 1 wherein said electrodes comprise silver metal.

8. An antimicrobial device according to claim 1 wherein said locking cap assembly further comprises a control circuit for alternating effective polarity of power applied to said electrodes.

9. An antimicrobial device according to claim 1 wherein said control circuits comprise counters and related electronics by which said control circuit is set into a sleep mode and awakened from said sleep mode in a predetermined cycle.

10. An antimicrobial device according to claim 1 wherein said sleeve part further comprises at least one antimicrobial is substance selected from a set of antimicrobial substances comprising chlorhexidine and silver sulfadiazine.

11. An antimicrobial device according to claim 1 wherein said sleeve part further comprises at least one antibiotic substance selected from a set of antibiotic substances comprising minocycline and rifampin.

12. An antimicrobial device according to claim 1 wherein the catheter is a central venous catheter.

13. An antimicrobial device according to claim 1 wherein the catheter is a thermodilution catheter.

14. An antimicrobial device according to claim 1 wherein said locking cap assembly comprises electronic circuits for monitoring battery voltage and current flow through said pair of electrodes and sensible indicators for signaling monitored status.

15. An antimicrobial device according to claim 1 wherein the control circuits comprise low drain integrated circuits which operate intermittently to prolong life of the primary power source.

16. An antimicrobial device for use with an indwelling catheter, said device comprising:
a jacket and sleeve subassembly comprising:
a sleeve portion comprising a sleeve which is adapted to be slidably disposed about an indwelling catheter which is configured to be displaced through an opening into a predetermined indwelling site within a body cavity, said sleeve portion comprising a pattern of a pair of electrically conductive wires disposed throughout said sleeve such that ions electrolytically displaced from one of the wires toward the other wire forms a guard against transport of biological materials along any portion of said sleeve which is to be disposed within said opening;
a jacket portion comprising a jacket for engaging a segment of the catheter for slidable displacement of the catheter within the jacket and sleeve subassembly such that at least a portion of the sleeve is to be disposed within the opening, and which comprises a pair of electrical connections for connecting with a pair of corresponding electrical connections associated with a power source by which ions are electrolytically displaced from the wires;
a cap subassembly comprising:
a power source and associated electronics for controlling rate and direction of electrolytic displacement of ions from said wires;
a mechanical connection by which said cap subassembly is releasibly affixed to said jacket and sleeve subassembly;
electronic monitoring circuitry for determining and indicating operational efficacy of said device, said circuitry comprising measuring and determining status of at least voltage of power source and current flow in said wires; and
the pair of electrical connections wherethrough said associated electronics communicates with said wires.

17. A method for using an antimicrobial device comprising the following steps:
providing a sleeve and jacket assembly comprising a sleeve part and a jacket part;
said sleeve part comprising a pair of spatially separated electrodes disposed in a predetermined pattern such that, when said sleeve part is at least partially disposed within an electrically conductive medium, ions eluted by electrolysis from one of said electrodes and attracted to the other of said electrodes creates an effective antimicrobial zone of influence within said medium about said electrodes;
said jacket and sleeve assembly cooperatively comprising a pathway through which a catheter is slidably disposed;
said jacket part further comprising extensions of each of said electrodes which communicate with a first electrical connector;
providing a locking cap assembly comprising a power source and a control circuit for applying power in a predetermined sequence and polarity to said electrodes;
said locking cap assembly further comprising a fitting, which releasibly but securely affixes said locking cap assembly to said sleeve and jacket assembly and further compressively affixes said sleeve and jacket assembly to an associated indwelling catheter disposed in said pathway, and a second electrical connector which completes an electrical circuit to said electrodes through said first connector when the locking cap assembly is affixed to said sleeve and jacket assembly;
providing an insertable catheter;
displacing a predetermined length of the catheter through an opening into a desired indwelling site within a body cavity;
slidably affixing said sleeve and jacket assembly about the indwelling catheter and inserting at least a portion of said sleeve through said opening;

securely affixing said locking cap assembly to said jacket and sleeve assembly and therethrough to said indwelling catheter to thereby securely affix the indwelling catheter to the sleeve and jacket at the opening; and applying power to said electrodes from said power source to provide an effective antimicrobial zone of influence thereby.

18. A method according to claim 17 comprising the further step of removing said installed antimicrobial device from the opening and from said indwelling catheter and replacing a freshened antimicrobial device comprising at least a fresh jacket and sleeve assembly about said indwelling catheter and into the opening.

19. A method according to claim 17 comprising the further step of removing a previously installed power source and installing a next installed power source.

20. A method according to claim 17 comprising the further step of emitting a detectable signal upon detection, by said control circuits, of an operational anomaly of said device.

21. A method for using an antimicrobial device according to claim 17 comprising the additional steps of:

providing suture wings affixed to said jacket and sleeve assembly; and suturing said suture wings in place to secure the catheter relative to the opening.

* * * * *